United States Patent [19]

Bailey

[11] 4,253,832

[45] Mar. 3, 1981

[54] DENTAL HANDPIECE

[75] Inventor: Ronald L. Bailey, St. Peters, Mo.

[73] Assignee: Young Dental Manufacturing Company, Inc., Hazelwood, Mo.

[21] Appl. No.: 953,473

[22] Filed: Oct. 23, 1978

[51] Int. Cl.³ .............................................. A61C 1/05
[52] U.S. Cl. ..................................... 433/115; 433/133
[58] Field of Search ................... 32/27, 59, 26, 29, 30, 32/31, 48; 433/115, 125, 126, 133

[56] References Cited

U.S. PATENT DOCUMENTS

| 517,248 | 3/1894 | Stanbrough | 32/27 |
|---|---|---|---|
| 2,025,779 | 12/1935 | Roelke | 433/133 |
| 2,469,261 | 5/1949 | Cooper | 32/59 |
| 2,813,337 | 11/1957 | Uhler | 32/27 |
| 2,943,343 | 7/1960 | Jankelson | 32/31 |
| 3,436,830 | 4/1969 | Richmond | 32/59 |
| 3,472,045 | 10/1969 | Nelsen et al. | 32/59 |
| 3,769,707 | 11/1973 | Condon | 433/133 |

Primary Examiner—F. Barry Shay
Assistant Examiner—John J. Wilson
Attorney, Agent, or Firm—Rogers, Eilers & Howell

[57] ABSTRACT

A dental handpiece having a cross head with one end capped and the other end open, a driven gear in the capped end having a thrust bearing against the cap, and a fixed bearing extending from the gear to the open end with a driven shaft rotatably mounted in the bearing; a threaded socket in the driven shaft to receive the complementary attaching means on a dental tool, a cylindrical recess in the open end to receive a flange on the tool and grooves in the driven shaft to restrain travel of abrasive from the open end toward the closed end thereof, the bearing being long enough to give complete bearing support for the rotating mechanism.

10 Claims, 1 Drawing Figure

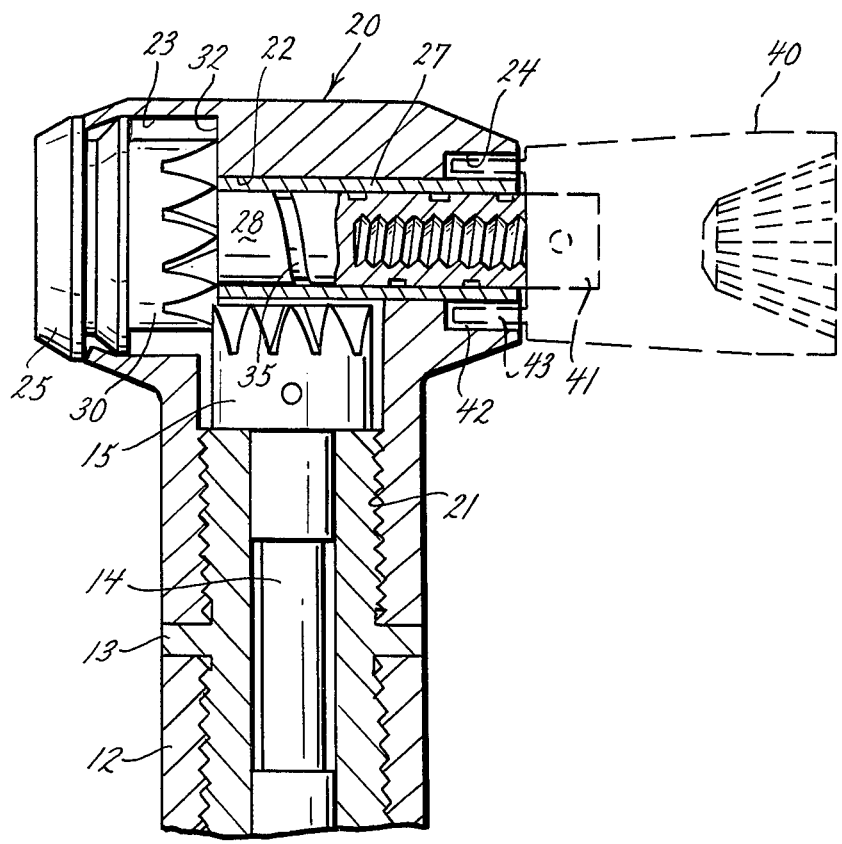

DENTAL HANDPIECE

BACKGROUND OF THE INVENTION

A broad object of the invention is a compact dental handpiece or prophylaxis angle that minimizes the passage of material such as abrasives from the open or tool-receiving end to the rotating parts and closed end.

Other dental handpieces are shown in Richmond U.S. Pat. No. 3,436,830 and Bailey U.S. Pat. No. 4,014,099, and the art cited in them. Prior art has suggested the disposition of the driven gear toward the closed end of the cross head, as witness Fernald U.S. Pat. No. 1,170,523 and Heatherington U.S. Pat. No. 3,978,586. Fernald has two shaft bearings that must be aligned, and does not have any thrust bearing arrangement. Heatherington has only a sketchy showing and merely suggests location of the driven gear at the closed end of the head bore. Cooper U.S. Pat. No. 2,469,261 purports to illustrate an arrangement by which a rubber cup can seal by compression, but the disclosure is of an arrangement different from the one here proposed in that, among other things, the driving mechanism between the shaft and the rubber cup is part of the same mechanism that is supposed to give the sealing arrangement.

Objects of the present invention therefore include broadly the arrangement of the cross head for a dental handpiece that minimizes the possibility of having granular or abrasive material reach the moving parts where it could abrade them. The objects also include the provision of a single cylindrical bearing for the driven shaft that has a close fit with the shaft and a long path between its ends, to make a difficult path for the abrasive or liquid materials between the open and closed ends of the head. Also the single long bearing provides a very stable high-speed shaft, and does not require the alignment of multiple bearings to support the shaft. It will prevent irregular rotary motion of the shaft and of the dental instrument attached to it.

Another object of the present invention is to provide a cross head for a dental handpiece wherein the end thrust applied to the dental instrument is taken by the bearing of the driven shaft against a fixed cap at the closed end of the cross head and particularly where it is taken by the back face of the driven gear.

Further objects include the construction of a dental handpiece with a minimum number of parts.

The drawing represents a diametrical cross section of the upper part of the handpiece or prophylaxis angle with a typical dental instrument to be attached thereto shown in dashed lines.

DESCRIPTION OF THE PREFERRED EMBODIMENT

The dental handpiece or prophylaxis angle of the present invention comprises a sleeve 12 shown broken away adjacent its outer end. This showing does not include the extended handle portion broken away as illustrated. The drawing is enlarged, a typical diameter of this outer end being about 9/32" (0.714 cm.). The sleeve 12 is internally threaded at its end to receive a double-ended threaded drive shaft bearing 13 that is tubular to receive a drive shaft 14. A drive gear 15 is fixed to the outer end of the drive shaft and is rotated by the shaft. The end of the gear 15 bears on the end of the drive shaft bearing 13.

A cross head 20 has a longitudinal bore 21 with an internally threaded end mountable over the projecting externally threaded end of the bearing 13. The bore 21 receives the gear 15. The head can thus be removed from the handle by being unscrewed, the gear 15 being capable of passing through the threaded opening. The head 20 also has a transverse counter bore 22 into which the bore 21 connects. This counter bore 22 at the left (FIG. 1) has an enlargement 23 and at its right end has an enlargement 24. The end of the bore at the left of the drawing is closed by a cap 25. The cap is peripherally grooved to be fixed in place by having the rim of the recess 23 swedged over into the groove. The capped end of the bore is here designated as the closed end.

The transverse bore 22 receives a long fixed cylindrical bearing 27, that extends from a recess 23 to the opposite or open end of the head 20. It projects across the enlarged bore 24 at that end. It is designed to be long for a purpose to appear.

A driven shaft or burr tube 28 is fitted within the bearing 27 with a close rotating fit, and is secured to a driven gear 30 within the bore enlargement 23. The outer (left, FIG. 1) end of the gear 30 and the inner face of the cap 25 have flat interfaces that provide a thrust bearing for the driven gear assembly and the dental tool. The cap 25 also seals the end of the head 20. The teeth on the driven gear 30 are bevelled, and the hub inside the teeth abuts the end surface 32 of the bore enlargement 23 and the end of the bearing 27. Thus the gear 30 and the burr tube 28 are retained rotatably in the head 20 between the cap 25 and the surface 32, with the driven gear 30 meshing with the driving gear 15.

The burr tube shaft 28 has a threaded socket to receive dental tools or instruments to be operated by the handpiece.

Preferably the burr tube or driven shaft 28 is provided on its outer surface with spiral grooves 35 for a purpose to appear. These grooves open into the counterbore enlargement 23 at one end and into the opposite end of the burr tube.

This dental handpiece is adapted to be used with all of the usual kinds of dental tools or instruments required by dentists such as burr tubes, rubber cups, disk holders and the like. A preferred form of instrument is illustrated in dashed lines in FIG. 1. As such, it is not a part of the present application, being the subject of a separate application.

The illustrated dental tool comprises a rubber cup 40 of typical material and outer shaping. The rubber cup is permanently mounted upon a metal core 41 that projects from it and has external threads by which it is attached to the internal threading of the shaft 28.

In the illustrated rubber cup, there is a flange 43 of the flexible rubber or plastic material, cylindrical in shape and designed to fit within the cylindrical groove 4 formed by the enlargement 24 of the counterbore 22 and the outside of the bearing 27. Other types of dental tools, such as burrs, disk holders, etc. can also be used, with or without the flexible flange seals 43.

USE

In use, the dental handpiece is held by the dentist, usually with his hand engaging the portion of the sleeve 12 that is not shown, the portion 12 as illustrated and the head 20 being small enough readily to fit within the spacings within the mouths that are to be treated.

With an appropriate instrument such as the rubber cup 40 mounted on the burr tube 28, the dentist starts the driving motor for the shaft 14. This rotates the gear 15 which is in mesh with the driven gear 30 causing the shaft 28 to rotate and with it the instrument 40. Typical shaft speeds are 1500 r.p.m.

The instrument 40 is pressed against the teeth of the patient, which applies a thrust force toward the left in FIG. 1. This force is transmitted to and accommodated by the engagement of the end of the driven gear 30 and the inner surface of the cap 25, which have mutual bearing interfaces. The design of the end cap and its use as the thrust bearing provides a means to reduce the axial length of the head as well as providing a larger thrust bearing surface.

The long bearing 27 supporting the shaft 28 affords an extended single bearing surface that can be made to extremely close tolerances. This affords steady support for the shaft as well as a long and restrictive path resisting passage of foreign matter from the open to the closed end of the head. It also minimizes eccentricities and irregularities that can cause uneven rotation at the high speeds encountered in this type of equipment. Heretofore one relatively short bearing, or two bearings, have been used. If two, one is usually near the open end of the head and the other near the other end. Two bearings have the difficulty of maintaining the two in appropriate close alignment, absent which abnormal wear quickly destroys the head.

Furthermore, with the equipment heretofore provided, the usual arrangement has the driven gear near the open end of the head of the handpiece. This means that an additional thrust bearing is required. The long bearing 27 and the disposition of the driven gear 30 away from the open end of the head reduce the chances for the abrasive material to insinuate itself into the gearing where it can cause excessive wear. Yet the arrangement affords the foregoing advantages without increasing the overall dimensions of the handpiece.

It will also be observed that the tool 40 has a shank threaded into a closed-ended socket of the driven shaft 28, such that the abrasive material cannot pass around the threads of the instrument to arrive at the gearing. In conventional handpieces burr tubes are fitted through a cylindrical bearing to the closed end of the head in such fashion that abrasive material can pass completely along the burr tube shaft and out into the recesses wherein the gearing is located.

In the present arrangement, if there is any wear that permits the driven gear to be moved toward the closed end of the head, the gear teeth are not driven tighter together in contrast to the conditions where the driven gear is located toward the open end of the head as shown in applicant's earlier U.S. Pat. No. 4,014,099.

It will further be observed that fewer parts are required for the present dental handpiece than are required in former handpieces such as in applicant's prior patent above referred to. With the gearing disposed toward the open end of the head as illustrated in the prior patent, it is essential to have a removable thrust member to position the driven gear accurately in mesh with the driving gear, and a removable cap for the open end. This not only adds parts, but makes it virtually impossible to provide the flanged arrangement as shown on the rubber cup 40 in dashed lines herewith. That particular flange 43 is sufficiently resilient that when the rubber cup 40 is spun at high speed by the gearing, the flange will be moved out under centrifugal force into engagement with the outer walls of the bore 24 providing a seal thereat, all as is explained in a co-pending application, filed substantially concurrently herewith.

The spiral groove 34 has its lead running in the direction to retard the travel of abrasive from the open end toward the closed end of the shaft.

What I claim is:

1. In a dental handpiece: a cross head having a bore therein with an open end and an opposite closed end, the open end being adapted for receiving dental tools; a cap fixed in position on the cross head, and closing the closed end of the bore; a driven gear adjacent the cap with the gear teeth facing the open end of the cross head bore; bearing inter-surfaces between the gear and the cap for thrust bearing; a driven shaft connected to the driven gear to be rotated thereby and extending therefrom to adjacent the open end; a tubular bearing fixed on the head, extending from the driven gear to the open end; said driven shaft being rotatably supported in the tubular bearing; and means on the driven shaft for mounting thereon of a dental tool, the cap receiving thrust load from the driven gear, the driven gear receiving thrust loads from the driven shaft, and the driven shaft being adapted to receive thrust loads from the dental tool, whereby the last named thrust loads are delivered to the cap, the cross head having a second bore at its open end of greater diameter than the tubular bearing, a cylindrical recess formed between the tubular bearing and the second bore wherein a flange on a dental tool can be received.

2. In the handpiece of claim 1, the driven gear having its teeth facing toward the open end of the bore, and a driving gear having teeth meshed with those of the driven gear.

3. In the handpiece of claim 1, the tubular bearing extending to the open end of the cross head, a cylindrically-walled recess around the bearing adjacent the open end, and a recess in the driven shaft to receive an attachment for a dental tool.

4. In the handpiece of claim 1, the tubular bearing extending to the open end of the cross head, a cylindrically-walled recess in the cross head of greater diameter than the tubular bearing diameter around the end of the bearing, to receive a flange of a dental tool, a closed end threaded recess in the driven shaft to receive a threaded extension on a dental tool.

5. The structure of claim 1 wherein the cap has locking means on the periphery of the cap, and the cross head has means at the closed end of the bore to interact with the locking means to lock the cap to the cross head.

6. The structure of claim 5 wherein the cross head bore comprises a first section and a second section, the second bore section having a larger diameter than the first bore section, the gear being housed within the second bore section, the gear being axially aligned with the first section, and the gear having a diameter greater than the diameter of the first bore section.

7. The structure of claim 6 wherein the tubular bearing extends within the first bore section towards the gear no farther than the junction of the first section and second section.

8. The structure of claim 1 wherein the cap has a peripheral groove, and the cross head has a rim fitted into the peripheral groove to hold the cap fixed to the cross head.

9. The structure of claim 1 wherein the cross head is a single member.

10. The structure of claim 1 wherein the shaft is straight and rigid; and further comprising means for repelling passage of material from the open end toward the closed end, comprising a spiral groove extending about the periphery of the shaft.

* * * * *